United States Patent [19]

Baugh

[11] Patent Number: 4,656,038

[45] Date of Patent: Apr. 7, 1987

[54] ANIMAL REPELLENT AND METHOD OF MANUFACTURE OF SAME

[75] Inventor: Clarence L. Baugh, Lubbock, Tex.

[73] Assignee: BioGenesis Laboratories, Inc., San Antonio, Tex.

[21] Appl. No.: 700,406

[22] Filed: Feb. 11, 1985

[51] Int. Cl.$^4$ .................... A01N 43/64; A01N 59/02
[52] U.S. Cl. ........................ 424/164; 424/93; 424/131; 424/162; 514/920
[58] Field of Search .............. 424/93, 131, 162, 164; 514/920, 918

[56] References Cited

U.S. PATENT DOCUMENTS

| | | | |
|---|---|---|---|
| 2,547,722 | 4/1951 | Stewart | 248/472 |
| 2,694,669 | 11/1954 | Baldwin et al. | 424/131 |
| 2,768,958 | 10/1956 | Stewart et al. | 424/131 |
| 2,977,250 | 3/1961 | Brysson et al. | 424/131 |
| 3,258,395 | 6/1966 | Shibe | 514/64 |
| 3,678,109 | 7/1972 | Knowles | 514/920 |
| 3,689,566 | 9/1972 | Knowles | 568/326 |
| 3,697,594 | 10/1972 | Knowles | 564/452 |
| 3,764,682 | 10/1973 | Knowles | 514/377 |
| 4,169,898 | 10/1979 | Haase et al. | 514/675 |
| 4,388,303 | 6/1983 | Allan | 514/920 |
| 4,388,352 | 6/1983 | Allan et al. | 427/391 |
| 4,469,613 | 9/1984 | Munteanu et al. | 424/22 |
| 4,477,433 | 10/1984 | Hultman | 424/93 |

OTHER PUBLICATIONS

G. G. Allan et al, "Reduction of Deer Browsing of Douglas—Fir (*Pseudotsuga Menziesii*) Seedlings by Quadrivalent Selenium", *Forest Ecology and Management*, vol. 7, (1983/1984), pp. 163–181.

*Primary Examiner*—Ronald W. Griffin
*Attorney, Agent, or Firm*—Dula, Shields & Eggert

[57] ABSTRACT

A composition of matter for repelling animals comprising the mixture of a metallic metal, a quantity of a soil that has been extracted from the earth, a nutrient source, and water. The soil is the type having a plurality of metallic metal metabolizing organisms thriving therein. The metallic metal is an ionic form of selenium. The nutrient source is a carbohydrate. In particular, the nutrient source can be lactose. The composition of matter further comprises a nitrogen source, such as tryptone. The composition may also include a quantity of tetrahydrofloate.

25 Claims, No Drawings

ANIMAL REPELLENT AND METHOD OF MANUFACTURE OF SAME

TECHNICAL FIELD

The present invention relates to compositions of matter that repel animals from desired locations. More specifically, the present invention relates to the compositions of matter that produce a dimethylated or methylated odor. The present invention also relates to methods of manufacturing such a composition of matter.

BACKGROUND ART

During stand development of conifers like Douglas fir, animals cause the greatest economic damage. Usually the animals browse and clip the stems and foilage of seedlings and saplings; while occasionally root cutting, budding, barking, trampling, and pulling of seedlings occur. Either the seedlings are killed or their growth is markedly suppressed by the browsing of big game (deer, bear, elk, and the like), hares and rabbits, grouse and other birds, beaver, gophers and other small rodents, domestic stock, and porcupines.

Four principal approaches are available for avoiding or controlling animal-caused damage to forest trees and their seedlings:
 (1) reduce the animal population;
 (2) exclude the animals from the plants mechanically.
 (3) repel the animals from browsing; and
 (4) alter silviculture practices.

Mechanical protection is the best in terms of damage prevented, but it is among the most expensive safeguards. Silviculture practices include (a) planting resistant species, (b) planting larger seedlings, (c) planting faster growing species, (d) removing and controlling other available food supplies in the plantation which might attract animals, and (e) cutting and replanting in arrangements which deter browsing.

Chemical repellents which affect either odor or taste are of two kinds-systemic and contact. A systemic repellent is applied to the foilage, roots, or soil (in the root zone), is absorbed in to the plant, and is translocated to all parts of the plant. A contact repellent is applied to the foilage and stems of plants and remains on the surface of the plants to treat them. Two common contact repellents are tetramethylthiuram disulfide and zinc dimethyldithiocarbamate cyclohexamine. When used with conifers, these repellents are usually either sprayed onto the plants at the nursery or the plants are dipped prior to planting. Both are usually applied in 10% concentration in a water solution containing latex adhesives, thickening agents, and defoaming agents. Other contact repellents include a putrified fish fraction (PFG), fermented eggs (EV repellent), and human hair.

Systemic repellents have been used extensively in the prior art. Rediske and Lawrence investigated induced animal repellency by using selenate compounds as systemic or contact repellents. 8 *Forest Science*, Vol. 2, at 142-148 (1962). Sodium selenate applied as surface coating (5,000 ppm Se) was an effective repellent; in fact, is more effective than the standard tetramethylthiuram disulfide contact repellent. As a systemic repellent, however, the experiments of Rediske and Lawrence showed that selenate was a failure. At the maximum allowable concentration in Douglas firs tested, the selenate did not repel animals from browsing.

U.S. Pat. No. 4,388,303, issued June 14, 1983, to George G. Allan, disclosed a method to reduce animal browsing damage to plants. This method comprised the step of inducing a nonphytotoxic dosage of selenium into the foilage of plants at a level sufficient to repel animals. The selenium is systemically absorbed into the plant after application of the surrounding soil in the root zone. By this technique, the roots absorb the selenium and translocate it to the foilage. This technique repelled animals by causing the leaves and foilage of the plants to be distasteful to the browsing animals.

Unfortunately, the prior art methods of utilizing selenium to discourage the browsing of animals was filled with problems. First, a relatively large quanity of selenium compounds was required to induce this systemic absorption. Secondly, insufficient doses, this system absorption of selenium could cause death, rather than discouragement, in certain types of animals. Thirdly, many types of plants are not suited to absorb the chemical selenium. In U.S. Pat. No. 4,388,303, it was believed that the systemic absorption of selenium was non-phytotoxic when the dosage level caused less than one-third of the seedlings to be killed.

The present invention, on the other hand, produces the beneficial effects of dimethyl selenide, without causing these disastrous effects. Through a non-systemic method of producing dimethyl selenide, the browsing animals are strongly are discouraged from entering a newly forested area. Additionally, the deterent effect is created without the destruction of damaging of even a small portion of the plant life in the area treated by the present method.

It is an object of the present invention to provide an animal repellent that effectively prevents the intrusion of many types of animals into newly planted or newly forested areas.

It is another object of the present invention to provide an animal repellent that is safe to human, animal, or plant life.

It is still another object of the present invention that requires a minimum of supervision, maintenance, and installation labor.

It is still a further object of the present invention to provide a method of manufacturing the animal repellent that is highly productive and cost effective.

It is a further object of the present invention to provide an animal repellent that requires relatively low amounts of selenium to be introduced into the area to be protected.

These and other objects and advantages of the present invention will become apparent from a reading of the attached specification and appended claims.

DISCLOSURE OF THE INVENTION

The present invention is a composition of matter for repelling animals that comprises the mixture of a metallic metal, a quantity of a soil that has been extracted from the earth, a nutrient source, and water. The soil is of the type having a plurality of metallic metal metabolizing organisms included therein. The nutrient source is of a type that is suitable for maintaining the metallic metal metabolizing organism.

The metallic metal that is used in the composition of the present invention is an ionic form of a metal that may be selected from the group consisting from selenium, arsenic, gold, silver, tellurium, and mercury. Preferably, the metallic metal of the present invention is an ionic form of selenium.

The nutrient source is a neutral compound composed of carbon, hydrogen, and oxygen. This nutrient source can be selected from the group consisting of sugar, starches, dextrans, glycogens, celluloses and pentosans. Preferably, the nutrient source of the present invention is a sugar, namely, lactose. The composition of the present invention can further include the intermixture of a nitrogen source, such as tryptone. This composition can further include a quantity of tetrahydrofloate, a methyl group doner chemical, or vitamin B-12.

The present invention also comprises a non-systemic method of preparing such an animal repellent that comprises the steps of: (1) preparing a mixture of the metallic metal, the quantity of naturally-occurring soil, and the nutrient source; (2) adding water to this mixture; and (3) incubating the mixture and the water until the mixture produces dimethyl selenide. In this method, the metallic metal is preferably an ionic form of selenium. The chemical sodium selenite may be used as this ionic form of selenium source. As before, the nutrient source can be a carbohydrate.

The method of preparing the animal repellent of the present invention can further comprise the steps of preparing a second mixture having selenium, a naturally occuring soil and a nutrient source, and introducing the second mixture to the previously stated incubated mixture.

The method the present invention can further comprise the steps of adding a nitrogen source to the mixture, adding a methyl group doner chemical to the mixture, adding tetrahydrofloate to the mixture, or adding vitamin B-12 to the mixture.

An alternative technique of the present invention comprises: (1) mixing a selenite broth with a soil extracted from the earth; (2) incubating the mixture of the selenite broth and the soil for a finite period of time; and (3) distributing the incubated mixture about the area frequented by the undesired animals. As used herein the selenite broth comprises a nitrogen source, a carbohydrate source, a selenium source, and water. This method further includes packaging the incubated mixture prior to the step of distributing. This step of distributing includes the distribution of the packages of the incubated mixture. Ideally, the packages are made of an odor porous material, such as latex.

Another embodiment of the present invention comprises the steps of: (1) adding a plurality of selenium metabolizing organisms to a quantity of earth-extracted soil; (2) mixing metallic selenium or derivatives thereof with the organisms in the soil; (3) mixing a nutrient solution with the selenium or derivatives and the organisms in the soil; and (4) incubating the mixture of the selenium or derivatives, the organisms, and the soil for a finite period of time. This method further includes the step of sterilizing the soil prior to the step of adding the organisms. Charcoal may also be mixed with the organisms, the selenium and the soil. The finite period of time is continued until dimethyl selenide is produced. The nutrient solution comprises a carbohydrate and water.

BEST MODE FOR CARRYING OUT THE INVENTION

The present invention is a non-systemic animal repellent and a non-systemic method of manufacturing and using such animal repellent. The composition of this animal repellent comprises the mixture of a metallic metal, a quantity of naturally-occurring soil, a nutrient source, and water. It is the mixture of each of these components of the composition that produces a methylated or dimethylated smell. The smell produced by this mixture effectively repells certain animals from a desired location. It is important that this smell is prduced without the need for systemic absorption of selenium.

In the best mode for carrying out the present invention, the nutrient source, the metallic metal, and the water is provided by a selenite broth. Selenite broth has commonly been used in the past to enhance the growth of Salmonella. The selenite broth operates by inhibiting the growth of other organisms while allowing the Salmonella to grow. DIFCO TM and BBL TM are two commonly used types of selenite broth. The selenite broth used in the preferred embodiment of the present invention contains the following ingredients: 5 grams of tryptone per liter of broth; 4 grams of lactose per liter of broth; 4 grams of sodium selenite per liter of broth; and 10 grams of sodium phosphate per liter of broth.

The above-stated broth provides a number of the essential ingredients of the composition of the present invention. In particular, the selenite broth provides a metallic metal to the mixture in the form of sodium selenite. In this broth mixture, it would be easy to substitute organic selenium or selenate for the sodium selenite. The nutrient source is provided in the form of lactose in the selenite broth. Lactose is a slightly sweet dextrorotatory reducing disaccharide sugar. It should be noted here that many, many alternatives are available for the nutrient source of the composition of the present invention. Typically, the nutrient source can be selected from a group of neutral compounds composed of carbon, hydrogen and oxygen. This group would include sugars, starches, dextrans, glycogens, celluloses and pentosans. This group is known more generally, and referred to herein, as carbohydrates.

The tryptone in the selenite broth provides the nitrogen source to the compositions of the present invention. While tryptone is included within the commonly available selenite broth, there are many other sources of nitrogen that would be available and which could be used in the composition of the present invention. The nitrogen source enhances the growth ability of the selenium positive organisms in the composition of the present invention.

The sodium phosphate as used in the selenite broth is utilized for buffering capacity. The buffer is a substance that in solution is capable of neutralizing within limits both acids and bases and this acts to maintain the original hydrogen-ion concentration of the solution. The sodium phosphate/buffer as used in the selenite broth is not an essential requirement of the composition of matter of the present invention. The buffer may be used, however, to provide optimal pH balance.

The selenium broth, as described herein before, is added to a naturally-occurring soil. As used herein, a naturally-occurring soil is any productive soil that has not been sterilized of the living organisms contained therein. This naturally-occurring soil is a soil that has been extracted from the earth. It is important that the animal repellent of the present invention is prepared separate from the earth, rather than in combination with the earth as part of a naturally-occurring process. A naturally-occurring soil will have a population of soil microorganisms that will convert selenium into dimethyl selenide. Within this soil sample there will exist a larger number of microorganisms that do not convert selenium into dimethyl selenide. In a typical naturally occurring situation, the selenium-converting microorganism have no selective advantage over the non-converting microorganisms.

The selenite broth and the soil are agitated or stirred together so as to form a mixture. Water can be added before or after mixing the broth and the soil. It is also possible that the soil could contain sufficient water, in itself, to support the process of the present invention. After this mixture is created, the mixture is incubated for a finite period of time. The incubation period allows the selenium-converting microorganisms to sustain a desired amount of growth. During the incubation period, the selenite broth will support the growth of the selenium-converting microorganisms while inhibiting the growth of the non-converting microorganisms. As a result, the ratio of selenium-converting microorganisms to non-converting organisms (hereinafter referred to as "selenium positive organisms versus selenium negative organisms") is greatly increased. The incubation period is continued until dimethyl selenite is produced. In laboratory experiments, this incubation period is approximately three days.

This incubation period can be also identified as a "selective growth period". Prior to the present invention, it had been considered impossible to selectively enrich the population of selenium positive organisms because the production of dimethyl selenide from selenium does not give the microorganisms any known selective advantages. However, the use of the sodium selenite and/or all of its derivatives, with an appropriate energy source, and with a nitrogen source allows the dimethyl selenide producing microorganisms in the soil to grow and maintain a selective advantage over the selenium negative organisms. Once the selective growth period has been completed, metallic selenium or any other selenium compound is effective since it can be converted to dimethyl selenide if an appropriate energy source is available to the selenium positive organisms. The nitrogen source is not necessary once the growth of the selenium positive organisms is established.

The order of the conversion process is as follows: (1) sodium selenite, (2) selenium, (3) methyl selenide, and, finally, (4) dimethyl selenide. Either methyl selenide or dimethyl selenide will produce an odor that is offensive to certain types of animals. Laboratory experiments have indicated that this odor is offensive to deer, rabbits, mice, dogs, gophers, and prairie dogs. When this odor is maintained about a particular area, these types of animals are repelled therefrom. As a result, the composition of the present invention is effective as an animal repellent.

Once the mixture of the present invention has been prepared, it is then necessary to package this mixture so that it can be effectively transported and used in a desired location. One technique is to package the mixture of sodium selenite, the soil, the nutrient source, and the nitrogen source prior to the step of adding water to the mixture. This packaged mixture can then be transported and distributed in the desired location before the smell of dimethyl selenide would be produced. In other words, dimethyl selenide production will not occur until water is added, in one way or another, to the mixture. This mixture can be placed in water porous and odor porous packaging materials. After the mixture is placed in the desired location, the packages or mixture from the packages, can be watered naturally or artificially. Natural water could occur from rain, floods, dew, or variety of other ways. Artificial watering could be accomplished by irrigation, by sprinkling, or many other ways. After water is mixed with the mixture, dimethyl selenide production will occur in the near future.

An alternative technique is to package the incubated mixture of the selenium, the soil, the nutrient source, and the water. The incubated mixture can then be distributed about the area frequented by undesired wildlife. This technique would produce immediate dimethyl selenide odor effects. The incubation of this mixture could occur during the transportation and distribution stages of this method. The only requirement for the packaging would be that it be odor-porous. Specifically, latex can be used as the material for packaging the dimethyl selenide producing mixture.

A wide variety of metallic metals may be used in place of selenium, in the present invention. The group of metallic metals may include: selenium and its derivatives, arsenic, gold, silver, tellurium, and mercury. Each of these metallic metals will produce a dimethylated or methylated odor in conjunction with certain organisms in the soil. Specifically, it is believed that each of these metals, in their ionic form, will interact conveniently with the soil microorganisms and the other materials so as to produce an animal repelling smell. As a result, it is believed that these metallic metals would fall within the scope of the present invention.

The non-systemic method of producing the composition of the present invention can be inclusive of a variety of procedures. One such alternative procedure is to add a chemical so as to speed up the methylation process, to minimize incubation time, and to increase the total amount of dimethyl selenide production. Three different chemicals have been found suitable for providing such an effect. One such chemical is vitamin B-12. Vitamin B-12 is a red crystalline complex cobalt-containing cyano antianemic compound that is in part related chemically to porphin and is in part a nucleotide. Vitamin B-12 has shown itself to be effective in speeding up the methylation process. Another chemical that can be used is tetrahydrofloate. Additionally, any of a variety of methyl group doner chemicals may be used to speed up the methylation process. Methionine is an amino acid that is one example of such a methyl group doner chemical. By the inclusion of any of these chemicals with the mixture of the present invention, the repelling smell output can be greatly increased.

The method of the present invention may be further modified so as to provide for immediate and long-term release of dimethyl selenide. This can be accomplished by preparing a second mixture of the selenium source, the soul, and the nutrient source and introducing the second mixture to the incubated mixture. The second mixture is introduced to the incubated mixture or at about the time that dimethyl selenide production is occurring from the first mixture. Through this technique, the smell is produced from the mixture immediately and will be produced after the second mixtrue has been incubated in the field.

It is also possible to separate the selenium positive organisms from the rest of the mixture. In other words, a step is added to the method of the present invention in which the selenium positive organisms are separated from the incubated mixture at or about the time that dimethyl selenide production begins. Since the selenium positive organisms have attained their selective advantage at this time, the numbers of selenium positive organisms should be much greater than that found in the original soil sample. A variety of uses of the present invention becomes possible once the selenium positive organisms have been removed from the incubated mixture.

Once such method is to add the selenium positive organisms to an original mixture of the broth, the soil, the nutrient source, and the water. This can greatly increase the selective advantage of the selenium positive organisms and also provide near and long term effects. The selenium positive organisms that were introduced to the original mixture will produce a dimethyl selenide smell immediately. After incubation, the total mixture will produce more of the smell. By this technique, the mixture can be transported with a small amount of the smell emanating from the packaged mixture. Once it is distributed in the field, this lesser smell will still have deterrent effects on animals and, also, the smell will increase as the incubated portion attains its selective advantage.

Another technique whereby these separated selenium positive organisms can be used to their full advantage would involve the growth of the selenium positive organisms from an original sample. This technique would involve sterilizing a sample of soil such that the microorganisms contained in the soil sample are eliminated. The selenium positive organisms that have been separated from an original mixture can be added to this sterilized soil. In this manner, greater control and uniformity can be maintained relative to the growth of the selenium positive organisms.

A further technique is to take the separated selenium positive organisms and place them with selenium and/or its derivatives onto or mixed with charcoal. The charcoal would be integrally related to the growth process and the dimethyl selenide production process. Since charcoal absorbs odors, it could be used to regulate the release of the odors over a longer period of time. While charcoal is the primary odor absorbing material available, it is believed that any dimethyl selenide absorbing material could be included in this arrangement. Through this technique, the dimethyl selenide would have a rather slow release and even release over a period of time.

The composition of the present invention will continue to produce dimethyl selenide until the water or nutrient source is used up by the selenium positive organisms. Within the scope of the present invention, it would be possible to include a long-lasting/time release nutrient source so as to provide energy for long term dimethyl selenide production. Cellulose could be one type of nutrient source that could be employed within the mixture of the present invention so as to lengthen the time of dimethyl selenide production. Cellulose would take much longer to break down into glucose form. The cellulose is continually broken down by the selenium positive organisms and can be used as an energy source for a very long period of time.

The present invention provides a composition and a method of producing this composition that effectively repells animals from desired locations. In newly forested areas, deer are a continual problem because the deer will eat, gnaw on, and consume the newly emerging trees. A herd of deer can virtually destroy a newly forested area. By placing the composition of the present invention in such a newly forested area, the deer problem would no longer be of much concern. Deer are extremely offended by the smell of dimethyl selenide. It is unlikely that any deer would intrude into an area that was protected by such a smell.

The method of producing the composition of the present invention is relatively inexpensive and highly effective. As additional research is conducted on the composition of the present invention, it is believed that a variety of other applications as an animal deterrent will become evident. While the present invention is very effective in preventing and deterring animal intrusion, it has not adverse effects to the growth and viability of plant life. It also poses no hazard to human health by the consumption of the plant life protected by the composition of the present invention.

The foregoing disclosure and description of the invention is illustrative and explanatory thereof. In various changes in the details of the composition present invention or in the details of the method of generating the composition of the present invention, may be made within the scope of the appended claims without departing from the true spirit of the invention. The present invention should be limited by the following claims and their legal equivalents.

I claim:

1. A composition of matter for the repelling of animals comprising the mixture of:

an ionic form of a metal, said metal being selected from the group consisting of selenium, arsenic, gold, silver, tellurium and mercury;

a soil having a plurality of metallic metal metabolizing organisms included therein, said soil having been extracted from the earth;

a nutrient for said metallic metabolizing organisms; and water.

2. The composition of claim 1, said metallic metal comprising an ionic form of selenium.

3. The composition of claim 2, said ionic form of selenium comprising selenite.

4. The composition of claim 1, said composition further comprising a source of nitrogen.

5. The composition of claim 4, said source of nitrogen being tryptone.

6. The composition of claim 1, said nutrient being selected from the group of neutral compounds composed of carbon, hydrogen, and oxygen consisting of sugars, starches, dextrans, glycogens, celluloses, and pentosans.

7. The compositions of claim 6, said nutrient being lactose.

8. The composition of claim 1, said composition further comprising:

a quantity of tetrahydrofloate.

9. The composition of claim 1, said composition further comprising:

a methyl group doner chemical.

10. A method of preparing an animal repellent comprising the steps of:

preparing a mixture of an ionic form of selenium, a soil extracted from the earth having a plurality of metallic metal metabolizing organisms included therein, and a carbohydrate;

adding water to said mixture; and incubating the water-added mixture until said mixture produces dimethyl selenide.

11. The method of claim 10, further including the step of:

adding a nitrogen source to said mixture.

12. The method of claim 10, said ionic form of selenium being sodium selenite.

13. The method of claim 10, further including the steps of:

preparing a second mixture of said metallic metal, a naturally-occurring soil, and a nutrient source; and introducing said second mixture to the incubated mixture.

14. The method of claim 10, further including the step of:
adding a methyl group doner chemical to the mixture of said metallic metal, said soil, said nutrient source and said water prior to the step of incubating.

15. The method of claim 10, further including the step of:
adding a tetrahydrofloate to the mixture of said metallic metal, said soil, said nutrient source, and said water prior to the step of incubating.

16. The method of claim 10, further including the step of:
adding a Vitamin B-12 to the mixture of said metallic metal, said soil, said nutrient source, and said water prior to the step of incubating.

17. A method of repelling animals comprising:
mixing a selenite broth with a soil that has been extracted from the earth;

incubating the mixture of said selenite broth with said soil for a finite period of time; and distributing the incubated mixture about the area frequented by said animals.

18. The method of claim 17, said selenite broth comprising:
a nitrogen source;
a carbohydrate source;

a selenium source; and water.

19. The method of claim 18, said nitrogen source being tryptone, said carbohydrate source being lactose and said selenium source being sodium selenite.

20. The method of claim 17, further including the step of:
packaging said incubated mixture, said step of distributing comprising distributing the packages of said incubated mixture, said packages being odor porous.

21. A method of producing an animal repellent odor comprising the steps of:

adding a plurality of selenium metabolizing organisms to a soil;

mixing metallic sellenium or derivatives thereof with said organisms in said soil;

mixing a nutrient solution with said selenium or said derivatives and said organisms in said soil; and incubating the mixture of said selenium or said derivatives, said organisms and said soil for a finite period of time.

22. The method of claim 21, further including the step of:

sterilizing said soil prior to the step of adding said organisms.

23. The method of claim 21, further including the step of:

mixing charcoal with said organisms, said selenium, and said soil.

24. The method of claim 21, said finite period of time being until dimethyl selenide is produced.

25. The method of claim 21, said nutrient solution comprising a carbohydrate and water.

* * * * *